United States Patent [19]

Brown

[11] Patent Number: 5,299,565

[45] Date of Patent: Apr. 5, 1994

[54] PORTABLE NEBULIZER APPARATUS

[76] Inventor: James N. Brown, 513 Magnolia Dr., Tupelo, Miss. 38801

[21] Appl. No.: 962,930

[22] Filed: Oct. 19, 1992

[51] Int. Cl.[5] ............ A62B 7/06; A61M 16/00; F16K 11/00; G05D 11/02
[52] U.S. Cl. ............ 128/200.21; 128/203.25; 128/204.18
[58] Field of Search ............ 128/200.14, 200.21, 128/200.24, 203.12, 203.17, 203.25, 203.27, 203.29, 204.18, 205.11, 205.24, 205.25

[56] References Cited

U.S. PATENT DOCUMENTS

| | | | |
|---|---|---|---|
| 717,474 | 12/1902 | Jolman et al. | 128/200.21 |
| 2,181,421 | 11/1939 | Fahr et al. | 128/200.21 |
| 3,104,062 | 9/1963 | Mahon | 128/200.21 |
| 3,379,194 | 4/1968 | Biermann | 128/200.21 |
| 3,521,634 | 7/1970 | Goodyear et al. | 128/205.23 |
| 3,588,057 | 6/1971 | Breiling | 128/205.25 |
| 3,809,080 | 5/1974 | Deaton | 128/200.21 |
| 4,191,952 | 3/1980 | Schreiber et al. | 128/203.25 |
| 4,197,842 | 4/1980 | Anderson | 128/203.25 |
| 4,244,361 | 1/1981 | Neubert | 128/205.25 |
| 4,257,415 | 3/1981 | Rubin | 128/200.21 |
| 4,276,876 | 7/1981 | Hakkinen | 128/200.21 |
| 4,741,331 | 5/1988 | Wunderlich | 128/200.21 |

Primary Examiner—David A. Wiecking
Assistant Examiner—Kimberly L. Asher
Attorney, Agent, or Firm—Leon Gilden

[57] ABSTRACT

A portable breathing apparatus is arranged to permit utilization within an automotive vehicle by employing a portable compressor having a twelve volt cigarette lighter adapter plug operative through a nebulizer structure to permit admixing of fluid medicant relative to compressed air. The organization is arranged to further optionally include an oxygen tank directing oxygen through the nebulizer into an associated breathing arrangement for an individual.

2 Claims, 4 Drawing Sheets

PORTABLE NEBULIZER APPARATUS

BACKGROUND OF THE INVENTION

1. Field of the Invention

The field of invention relates to portable breathing structure, and more particularly pertains to a new and improved portable breathing apparatus wherein the same is arranged to permit utilization within a self-propelled vehicle.

2. Description of the Prior Art

Various breathing apparatus are available in the prior art and typically are arranged in a stationary orientation, wherein the instant invention attempts to overcome deficiencies of the prior art by providing for a portable compressor structure arranged to permit utilization with a self-propelled vehicle. Breathing apparatus in the prior art is exemplified by the U.S. Pat. Nos. 4,826,510; 4,671,270; 4,197,842; 4,917,081; and 3,800,819.

Accordingly, it may be appreciated there continues to be a need for a new and improved portable breathing apparatus as set forth by the instant invention which addresses both the problems of ease of use as well as effectiveness in construction and in this respect, the present invention substantially fulfills this need.

SUMMARY OF THE INVENTION

In view of the foregoing disadvantages inherent in the known types of breathing apparatus now present in the prior art, the present invention provides a portable breathing apparatus wherein the same utilizes a portable compressor arranged for mounting within a self-propelled vehicle. As such, the general purpose of the present invention, which will be described subsequently in greater detail, is to provide a new and improved portable breathing apparatus which has all the advantages of the prior art breathing apparatus and none of the disadvantages.

To attain this, the present invention provides a portable breathing apparatus arranged to permit utilization within an automotive vehicle by employing a portable compressor having a twelve volt cigarette lighter adapter plug operative through a nebulizer structure to permit admixing of fluid medicant relative to compressed air. The organization is arranged to further optionally include an oxygen tank directing oxygen through the nebulizer into an associated breathing arrangement for an individual.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved portable breathing apparatus which has all the advantages of the prior art breathing apparatus and none of the disadvantages.

It is another object of the present invention to provide a new and improved portable breathing apparatus which may be easily and efficiently manufactured and marketed.

It is a further object of the present invention to provide a new and improved portable breathing apparatus which is of a durable and reliable construction.

An even further object of the present invention is to provide a new and improved portable breathing apparatus which is susceptible of a low cost of manufacture with regard to both materials and labor, and which accordingly is then susceptible of low prices of sale to the consuming public, thereby making such portable breathing apparatus economically available to the buying public.

Still yet another object of the present invention is to provide a new and improved portable breathing apparatus which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an isometric illustration of the instant invention.

FIG. 2 is an orthographic view, taken along the lines 2—2 of FIG. 1 in the direction indicated by the arrows.

FIG. 3 is an orthographic top view of the nebulizer structure.

FIG. 4 is an orthographic view, taken along the lines 4—4 of FIG. 3 in the direction indicated by the arrows.

FIG. 5 is an orthographic top view of a modified nebulizer structure utilized by the invention.

FIG. 6 is an orthographic view, taken along the lines 6—6 of FIG. 5 in the direction indicated by the arrows.

FIG. 7 is an isometric illustration of the modified breathing apparatus as employed by the invention.

FIG. 8 is an isometric illustration of the organization mounted within a portable container.

DESCRIPTION OF THE PREFERRED EMBODIMENT

Figures 1, 2:
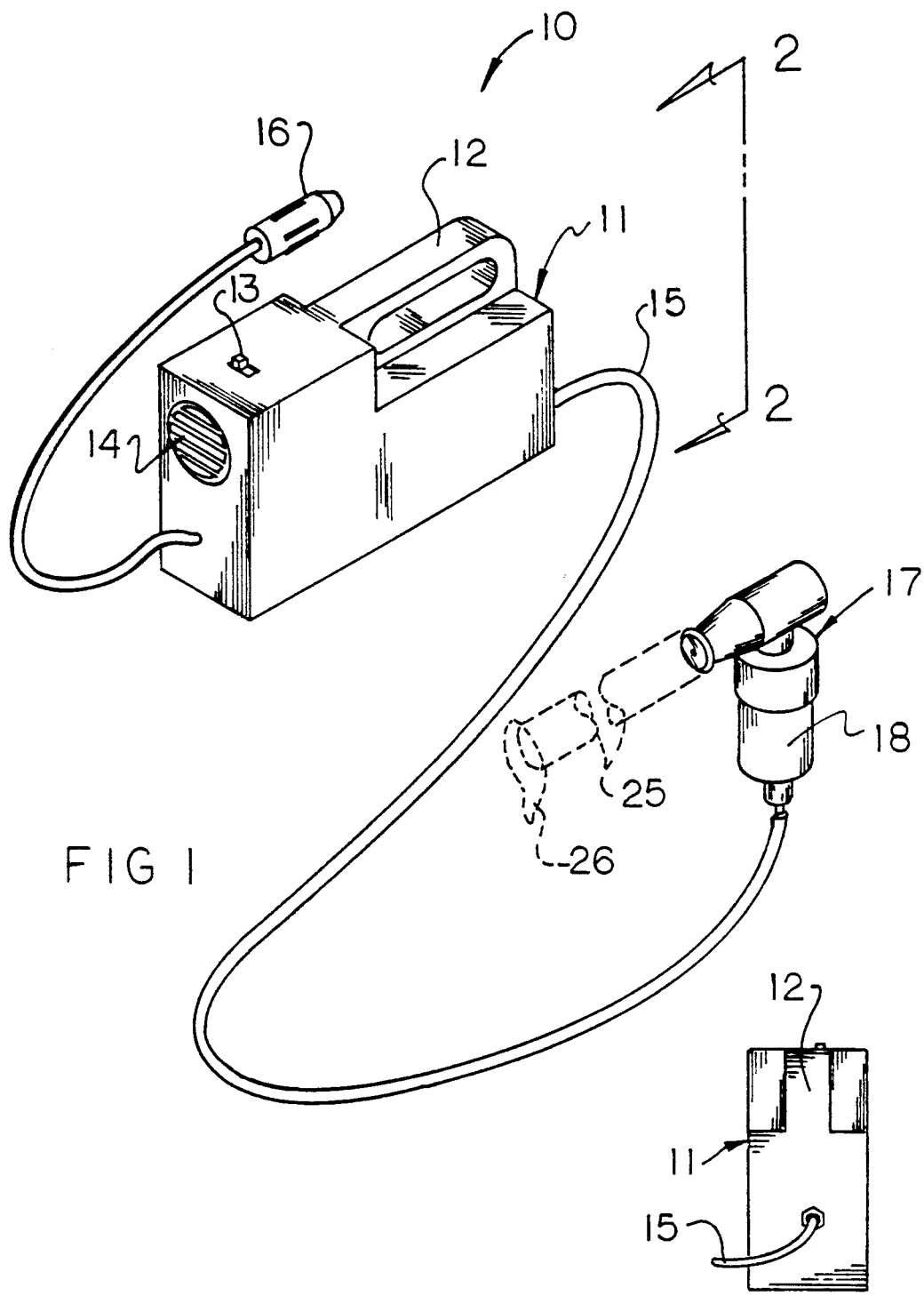
Figure 3:
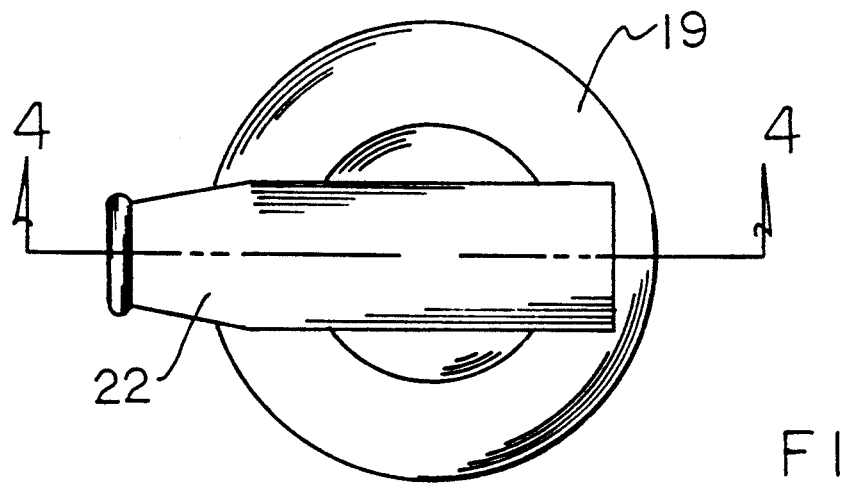
Figure 4:
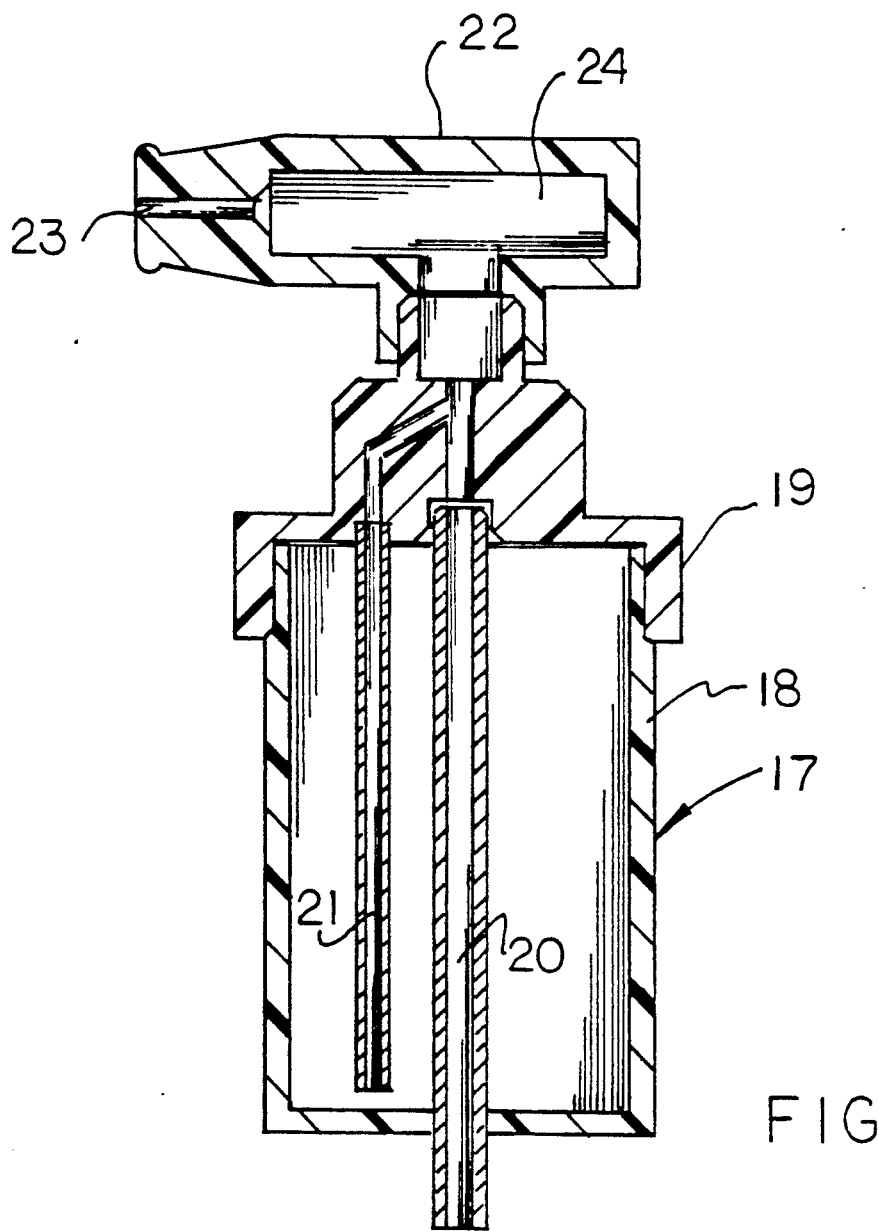

With reference now to the drawings, and in particular to FIGS. 1 to 8 thereof, a new and improved portable breathing apparatus embodying the principles and concepts of the present invention and generally designated by the reference numeral 10 will be described.

More specifically, the portable breathing apparatus 10 of the instant invention essentially comprises a portable air compressor 11 having a housing, to include a handle 12, an on/off switch 13, with an air inlet 14 directing pressurized air directed from the air inlet 14 in a compressed manner through a flexible outlet conduit 15. A twelve volt electrical plug adapter 16 (inasmuch as conventional vehicles utilize typical twelve volt systems where it is understood that any voltage relative to an associated vehicle may be utilized) includes a plug arranged for reception with an automotive cigarette lighter socket of conventional construction. The outlet conduit 15 is directed into a nebulizer 17, wherein the nebulizer is arranged to include a reservoir container 18 (see FIG. 4) to contain a fluid medicant as required, with a container cap 19 mounted removably relative to the container 18. The container includes a first conduit 20 directed through the reservoir container 18 into the cap 19, with a second conduit 21 in pneumatic communication with the first conduit 20 within the cap 19 projecting from the first conduit connection to a spaced relationship relative to a floor of the reservoir container 18 to thereby draw fluid by directing pressurized air through the first conduit 20 into the head member 22. The head member 22 includes an outlet nozzle 23, with a mixing chamber 24 receiving the fluid directed into the first conduit 20 from the second conduit 21 into the mixing chamber 24 and subsequently to the outlet nozzle 23, wherein a respirator conduit 25 is mounted to the outlet nozzle 23 and the respirator conduit 25 directed into a respirator mask 26 for mounting about an individual's nasal and mouth region as required.

Figure 5:
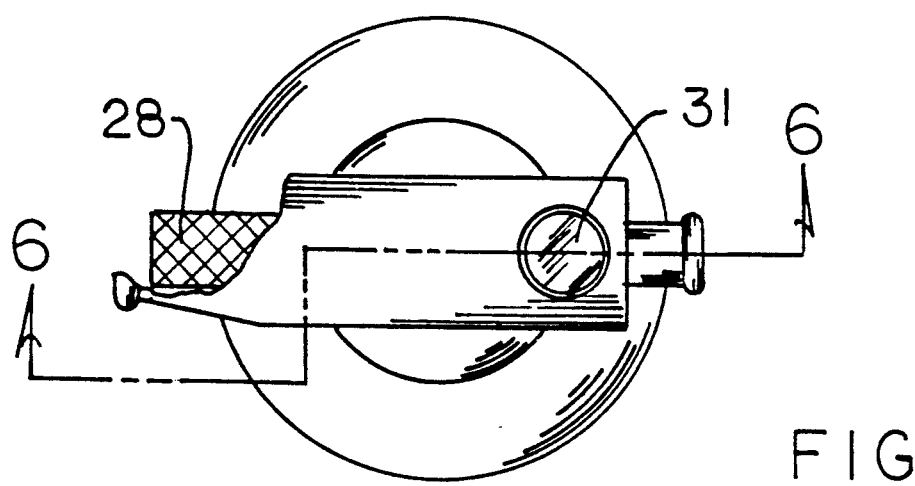
Figure 6:
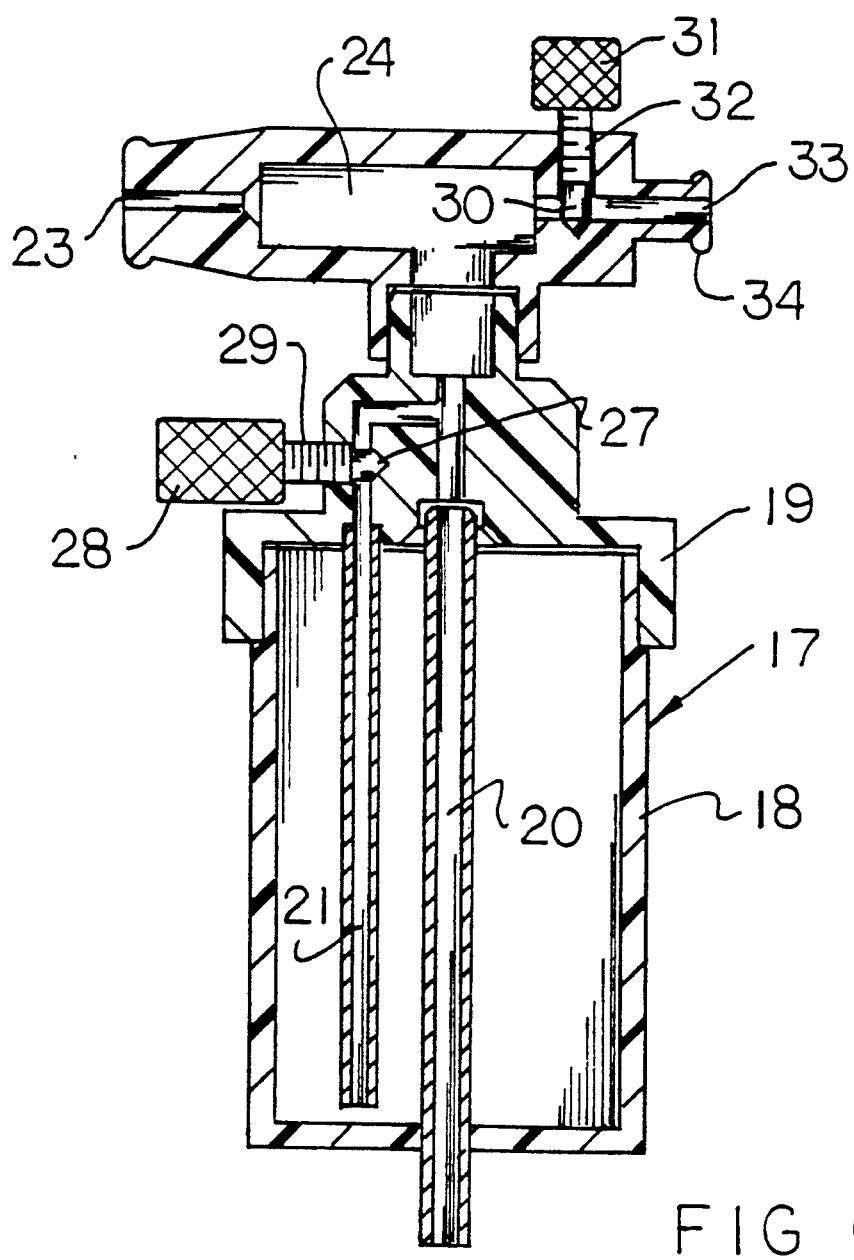
Figure 7:
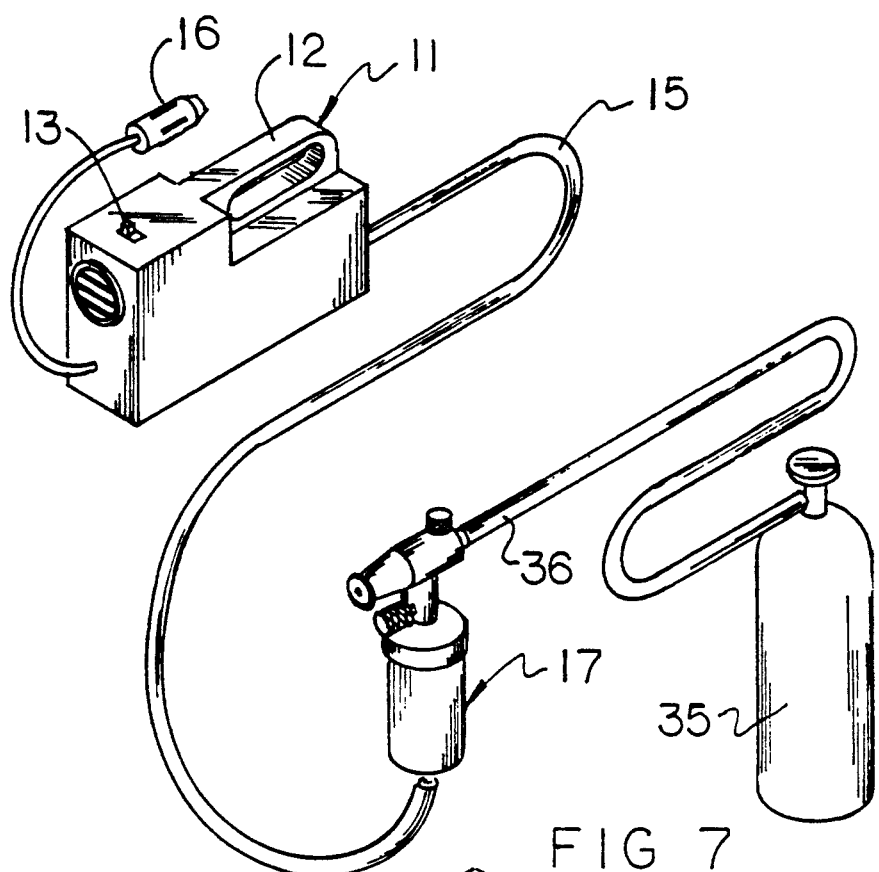

The nebulizer, as indicated in FIG. 5, is arranged to further include a first control valve rod 27 (see FIG. 6) projecting into the second conduit 21 to meter fluid flow therethrough, wherein the first control valve rod 27 includes a first control valve rod shank 29 threadedly directed into the cap 19, with a first handle 28 arranged for rotation of the first shank 29 to effect selective reciprocation of the first control valve rod 27 within the second conduit 21.

The cap 19 includes a third conduit 33 in pneumatic communication with the mixing chamber 24. The third conduit 33 is directed through a nipple 34 to receive an oxygen canister hose 36 directed from the nipple 34 to an oxygen canister 35 to permit admixture of oxygen within the atomized mixture within the mixing chamber 24 as required.

Figure 8:
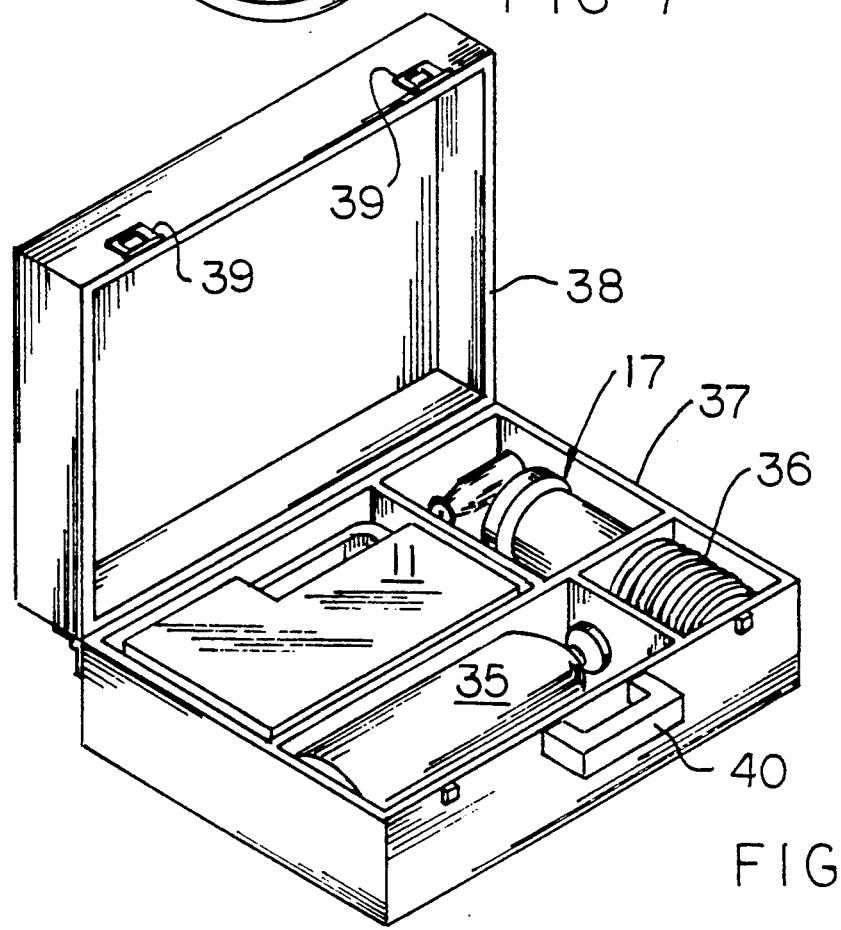

The FIG. 8 indicates the use of a compartmented container 37 arranged to receive the various components of the organization, with the container lid 38 having latch members 39 arranged to fixedly secure with latch components upon the container 37. A container handle 40 permits ease of portability of the organization for its transport and storage during periods of non-use.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the Unites States is as follows:

1. A portable breathing apparatus, comprising,
   an air compressor, the air compressor having an air inlet and an air outlet, the air outlet having a flexible outlet conduit extending therefrom, and
   the air compressor including an electrical conduit directed therein for directing electrical energy into the air compressor, and
   an electrical plug arranged for reception within a vehicular cigarette lighter mounted to a free distal end of the electrical conduit, and
   the flexible outlet conduit directed into a reservoir container and directed therethrough, and the reservoir container having a container cap, with the first conduit directed into the reservoir cap through the container in pneumatic isolation relative to the reservoir container, and
   a second conduit extending from the first conduit from within the container cap extending into the reservoir container, with the reservoir container having a container floor and the second conduit arranged in adjacency relative to the container floor, and
   a head member mounted to the container cap, the head member having an outlet nozzle, and a mixing chamber mounted within the head member in pneumatic communication with the first conduit, with a fluid medicant arranged for reception with the reservoir container for projection through the second conduit into communication with the first conduit when compressed air is directed through the first conduit from the outlet conduit and the air compresor, and
   the outlet nozzle includes a flexible respirator conduit mounted to the outlet nozzle and a respirator mask mounted to the respirator conduit, and
   first control means directed into the second conduit for adjusting fluid flow through the second conduit from the reservoir container, wherein the first control means includes a first control valve rod reciprocatably mounted into the second conduit, and the first control valve rod includes a first shank threadedly received within the container cap, and a first handle mounted to the first shank, wherein the first handle is positioned exteriorly of the container cap, whereupon rotation of the first handle effects reciprocation of the first control valve rod relative to the first conduit, and a third conduit directed into the head member into communication with the mixing chamber, and the third conduit including a third conduit nipple projecting exteriorly of the head member, and an oxygen canister, and an oxygen canister hose in pneumatic communication between the oxygen canister and the third conduit in surrounding relationship relative to the nipple.

2. An apparatus as set forth in claim 1 including second control means threadedly directed into the head member for adjusting fluid flow from the third conduit into the mixing chamber, wherein the second control menas includes a second control valve rod reciprocatably mounted into the third conduit, and a second shank threadedly directed into the second head mounting the second control valve rod thereon, and a second handle mounted to the second shank, with the second handle positioned exteriorly of the head member, whereupon rotation of the second handle effects reciprocation of the second control valve rod relative to the third conduit.

* * * * *